United States Patent [19]

Morrison et al.

[11] Patent Number: 4,976,886

[45] Date of Patent: Dec. 11, 1990

[54] PREPARATION OF ORGANOMETALLIC AND ORGANOBIMETALLIC COMPOUNDS

[75] Inventors: Robert C. Morrison; Terry L. Rathman, both of Gastonia, N.C.

[73] Assignee: Lithium Corporation of America, Gastonia, N.C.

[21] Appl. No.: 160,388

[22] Filed: Feb. 25, 1988

Related U.S. Application Data

[63] Continuation-in-part of Ser. No. 31,639, Mar. 30, 1987, abandoned.

[51] Int. Cl.$^5$ .................................................. C09K 3/00
[52] U.S. Cl. ............................ 252/182.3; 252/182.12
[58] Field of Search ............ 252/182.3, 182.14, 182.12; 502/153, 156, 157

[56] References Cited

U.S. PATENT DOCUMENTS

| | | | |
|---|---|---|---|
| 3,716,495 | 2/1973 | Hsieh | 502/153 |
| 3,822,219 | 7/1974 | Kamienski et al. | 502/153 |
| 3,886,089 | 5/1975 | Smith | 502/157 |
| 4,128,501 | 12/1978 | Smith et al. | 502/153 |
| 4,207,207 | 6/1980 | Sanchez et al. | 502/152 |
| 4,213,880 | 7/1980 | Knight et al. | 502/156 |
| 4,222,969 | 9/1980 | Fannin et al. | 502/152 |
| 4,342,708 | 8/1982 | Sakurai et al. | 502/156 |
| 4,429,054 | 1/1984 | Morrison | 502/157 |

OTHER PUBLICATIONS

Wakefield, "The Chemistry of Organolithium Compounds", pp. 198–199, Pergamon Press.

*Primary Examiner*—Edward A. Miller
*Attorney, Agent, or Firm*—Charles C. Fellows; Robert L. Andersen

[57] ABSTRACT

A process for producing organometallic compositions by reacting an organohalide with a mixture of two metals; one being an alkali metal, the other being selected from magnesium, calcium, barium and zinc in a hydrocarbon solvent containing 0.5 to 2.0 moles of a Lewis Base per mole of organohalide.

10 Claims, No Drawings

PREPARATION OF ORGANOMETALLIC AND ORGANOBIMETALLIC COMPOUNDS

CROSS REFERENCE TO RELATED APPLICATION

This application is a continuation-in-part of U.S. application Ser. No. 07/031,639, filed Mar. 30, 1987, and now abandoned.

This invention concerns a high-yield, economical process for producing novel, hydrocarbon soluble organo metallic compositions such as alkyllithium compounds, in a hydrocarbon solvent containing a limited amount of tetrahydrofuran (THF), other ethereal compounds or Lewis bases.

Alkyllithium compounds, particularly methyllithium (MeLi), are used as reagents in the preparation of pharmaceuticals and special chemicals. MeLi has been available commercially in diethyl ether solutions in the presence of an equivalent of lithium bromide (LiBr) formed as a by-product and remaining in solution as a complex with the methyllithium. A principle deficiency of this product is its high flammability due in part to the diethyl ether which is highly flammable and explosive in combination with oxygen and which contributes highly to the pyrophoric nature of the contained methyllithium. Although the presence of lithium bromide reduces the pyrophoric nature of methyllithium itself, the presence of lithium bromide interferes with certain applications of the methyllithium. There is evidence that the presence of lithium bromide may influence significantly the stereochemistry during the addition of methyllithium to carbonyl compounds. For these reasons it is often desirable to use an essentially halide-free methyllithium. However, the MeLi.LiBr complex has found in the past, and will in the future, many uses in organic syntheses, especially for those applications where stereochemistry is unimportant.

The pyrophoric nature of methyllithium taken together with the presence of diethyl ether has resulted in limited use of MeLi in diethyl ether. Moreover, other chemical routes or methyl Grignards are used.

Attempts were made in the 1970's to commercially market ethereal solutions of halide-free methyllithium prepared from methyl chloride and lithium shot. This resulted in the desired product containing not more than 5 mole percent lithium chloride based on contained methyllithium because the lithium chloride by-product has low solubility in diethyl ether. The slow reaction of methyl chloride with lithium shot resulted in incomplete reaction before filtration which resulted in poor product shelf life due to the post reaction Wurtz coupling of methyllithium and residual methyl chloride to form ethane and lithium chloride (LiCl). These diethyl ether solutions of methyllithium are marketed commercially even though they often degrade badly before use. Gilman and Gaj in Journal of Organic Chemistry 22, 1164 (1957) disclose preparing methyllithium from methyl chloride and lithium metal in THF. The THF/Li mole ratio was 9.8 indicating use of a large excess of THF. Thermal stability of these products was found to be poor even at 0° C. So in view of the thermal decomposition and the high cost of THF these products are not commercially feasible. There remains a need for a halidefree, thermally stable methyllithium solution in a relatively non-volatile solvent system and a process for producing such a product.

Using proton and lithium NMR analysis House, H. O. et al., J. Org. Chem., 32, 2481 (1967) and L. M. Seitz et al., J. Amer. Chem. Soc., 88, 4140 (1966) found that in diethyl ether methyllithium (MeLi) and dimethylmagnesium ($Me_2Mg$) form $Li_2MgMe_4$ and $Li_3MgMe_5$ complexes. L. M. Seitz et al. J. Organometallic Chem., 18, 227 (1969) disclose that in tetrahydrofuran only the 2:1 (Li:Mg) complex was observed. These workers prepared halidefree dimethylmagnesium via two methods: (1) the long, tedious Schlenk reaction which involves first the synthesis of methylmagnesiumbromide, the addition of dioxane to precipitate magnesium bromide followed by vacuum removal of the dioxane; (2) the process in which highly toxic and expensive dimethylmercury was stirred with excess magnesium to generate dimethylmagnesium.

Kamienski and Eastham in J. Organometallic Chem., 8, 542 (1967) disclose the reaction of an alkyllithium with a special activated magnesium chloride in diethyl ether which was not and is not commercially available as a route to dimethylmagnesium. Kamienski and Eastham in J. Org. Chem., 34 1116 (1969) disclose reaction of RLi with RMgX in diethyl ether to prepare dialkylmagnesium.

Most of the processes of the prior art are expensive, require handling of highly toxic reagents, employ commercially unavailable reagents and use highly flammable diethyl ether and thus are not commercially feasible processes. Unfortunately diethyl ether solutions of halide-free methyllithium are undesirably pyrophoric. The need remains for an inexpensive, commercial synthesis of halide-free dimethylmagnesium and halidefree, stable alkyllithium compositions.

The present invention provides stable hydrocarbon solvent-Lewis base, such as hydrocarbon-tetrahydrofuran, solutions of alkali metal alkyls and a method for producing stable hydrocarbon Lewis Base compositions of alkali metal alkyls containing not more than 5 mole percent lithium chloride based on the alkali metal alkyl content in which compositions the ratio of tetrahydrofuran to alkali metal alkyl is within the range of 0.05:1 and 2:1 and the hydrocarbon is a liquid aliphatic, alicyclic or aromatic hydrocarbon. These compositions are further stabilized by the presence of a small amount of an organometallic compound containing an alkyl group and a metal selected from group 2A, aluminum and zinc in the solutions. The method reacts an alkyl halide with an alkali metal in a hydrocarbon solvent containing not more than 2 moles of a Lewis Base, such as tetrahydrofuran, per mole of alkyl halide. When it is desired to produce these stabilized alkyl alkali metal compounds, mixtures of metals, one an alkali metal the other selected from group 2A, aluminum and zinc are reacted with an alkyl halide to produce compositions of variable metal content. For example, methyllithium stabilized with dimethylmagnesium can be varied from ratios of 1:99 to 99:1. Of course the dialkylmagnesium and alkyllithium can be separately produced and simply mixed together in the desired ratios. The preferred methyl halide, methyl chloride (MeCl) when reacted with an alkali metal produces a by-product, which is essentially insoluble. When organic bromides or organic iodides such as methyl bromide (MeBr) or methyl iodide (MeI) are employed, higher levels of by-product inorganic halide go into solution and actually improve the thermal stability of the complexed organometallic which is dissolved in a limited amount of Lewis Base and an aromatic solvent. For example, a $MeLi_{1.0}$-

.LiBr$_{0.69}$ complex dissolved in a limited amount of THF (THF/MeLi=1.65 mole ratio) and toluene was found significantly more thermally stable (about 8 times) at 40° C. than a comparable halide-free methyllithium solution in limited THF/toluene. As the number of carbon atoms in the alkyl group increases the amount of THF required to solubilize the organometallic compounds decreases. The solubility of methyllithium, even when stabilized with dimethylmagnesium or an inorganic halide is such that at least some of the solvent must be an aromatic solvent.

The process of the invention when producing alkali metal alkyls reacts an alkali metal preferably lithium metal, most preferably containing some sodium with an alkyl halide in a hydrocarbon solvent containing a small amount of a Lewis Base such as THF. The alkali metal is preferably finely divided and dispersed or slurried in an aromatic hydrocarbon containing tetrahydrofuran. The alkyl halide, preferably methyl or ethyl halide is added to the slurried lithium metal while the temperature is maintained below about 50° C.; preferably the temperature is maintained between 30° C. and 35° C. It is preferred to activate or condition the finely divided alkali metal, such as lithium metal and, if desired, magnesium metal, by stirring it or them together with a small amount of alkyllithium in the selected solvent for a short period before reaction with the alkyl halide. This appears to increase the reactivity of the lithium and magnesium metals. Typically the alkyl halide is added slowly to the alkali metal slurry with agitation as this facilitates control of the reaction temperature. The reactions involving an alkali metal are done under an inert atmosphere, preferably argon. The product is a tetrahydrofuran complex of alkyllithium, which may contain a corresponding dialkylmagnesium, in a hydrocarbon solvent.

A method or process variable having a great influence on yield is the amount of tetrahydrofuran present during the reaction. While the ratio of tetrahydrofuran to methyl halide may vary between about 0.05 and about 2.0 moles of tetrahydrofuran per mole of methyl halide, the preferred range is about 1.2 to 1.5 moles of tetrahydrofuran per mole of methyl halide when there is no magnesium present in the reaction. Surprisingly higher and lower levels of tetrahydrofuran (THF) tend to result in lower yields.

Organic halides useful in practicing this invention may be represented by the formula RX in which X is selected from the group of chloride, bromide and iodide and R is selected from the group of alkyl, cycloalkyl, $\alpha,\alpha$-alkylene, alkenyl and aryl groups. More specifically, R can be selected from the group of methyl, ethyl, n-butyl, sec-butyl, 2-ethylhexyl, n-octyl, cyclohexyl, 1,4-butylene, phenyl, cumyl, benzyl, tolyl, vinyl and crotyl groups. When desired mixtures of different organohalides can be employed to produce mixed organic groups in the products of this invention.

The liquid hydrocarbon solvents used in practicing this invention are typically selected from aliphatic hydrocarbons containing five to ten carbon atoms, alicyclics containing six to ten carbon atoms and aromatic hydrocarbons such as benzene, toluene, ethylbenzene, cumene and so forth.

Products of this invention of particular interest include solutions of lower alkyllithium compounds which if desired can contain stabilizing amounts of diorganometallic compounds such as dialkylmagnesium products or inorganic halides such as lithium bromide or lithium iodide. Thus, such compounds as methyl or ethyllithium are stabilized by small amounts of dimethyl- or diethylmagnesium, respectively. These compounds are useful as alkylating agents in the synthesis of pharmaceuticals and in other complex organic synthesis reaction sequences. These alkyllithium solutions containing a diorganometallic compound have improved stability, that is compounds such as methyllithium containing a stabilizing amount of dimethylmagnesium have a reduced tendency to precipitate methyllithium from solution and have a reduced tendency to metallate the aromatic solvents and thus do not release methane with accompanying increased pressure, which is undesirable.

The dialkylmagnesium/alkylmagnesium halides compositions of this invention have characteristics similar to the corresponding dialkylmagnesium compounds and are used for similar purposes such as alkylations and the like where Grignard agents are often used. In this respect these compounds, such as Me$_2$Mg/MeMgCl, react more completely than Me$_2$Mg as the presence of the chloride is believed to promote reaction of the alkyl groups and so, more completely reacting such alkyl groups in the Me$_2$Mg/MeMgCl compounds.

Methyllithium and dimethylmagnesium (Me$_2$Mg) are not hydrocarbon soluble. While the use of a limited amount of a Lewis Base, such as THF, solubilizes these organometallic compounds in hydrocarbon solvents, preferably aromatic solvents, the solutions containing only methyllithium tend to be unstable; methyllithium precipitates in certain cases, such as when cumene is the aromatic solvent, upon storage at low or elevated temperatures and metallates aromatic solvents under some storage conditions such as, at elevated temperatures. Surprisingly, inclusion of dimethylmagnesium in small amounts in the methyllithium solutions in a hydrocarbon solvent containing limited THF both stabilizes the methyllithium and increases its solubility thus, making possible more concentrated, stabilized solutions. It is possible to separately prepare dimethylmagnesium and methyllithium solutions and mix them together to obtain the stabilized compositions of this invention. However, it is much easier and simpler to prepare methyllithium solutions stabilized with dimethylmagnesium by using the mixed-two metal process of the present invention.

The present process employs a hydrocarbon solvent containing a limited amount of tetrahydrofuran (THF), other ethereal compound or Lewis Base. The novel organometallic products of the process are dissolved in these hydrocarbon solvents containing a limited amount of a Lewis Base such as tetrahydrofuran, methyltetrahydrofuran and so forth. The amount of THF varies from 0.05 to 2.0 depending on the alkyl group selected. Slightly more than one (1) equivalent of THF per alkyl group is used when the alkyl group is methyl with 1.2 to 1.5 THF equivalents being preferred. However, as the carbon content of the alkyl group increases less THF is required to solubilize the organometallic compound; when the alkyl group is ethyl only 0.5 to 0.7 equivalents of THF are required to solubilize ethyllithium and it is known that diamylmagnesium is hydrocarbon soluble without THF. Moreover n-propyllithium is known to be hydrocarbon soluble. Compositions of particular interest in pharmaceutical synthesis work are solutions of methyllithium; methyllithium hydrocarbon solutions solubilized by 1.2 to 1.5 equivalents of THF and stabilized by 7 to 8 mole percent or more of dimethylmagnesium are also useful in such complex organic synthesis operations.

A particular advantage of the present invention is that the compounds of the invention have been synthesized in high yield by way of a novel reaction sequence in a single reactor which involves gradual addition of an organic halide to a mixture of an alkali metal and a metal selected from magnesium, calcium, barium, aluminum and zinc in a hydrocarbon solvent containing a limited amount of tetrahydrofuran. The final product is obtained by filtration to remove unreacted metal and inorganic metal halide. The most important novel compositions synthesized via this general process are dimethylmagnesium and methyllithium/dimethylmagnesium compositions in which the ratios of the components in the latter product range from 1:99 to 99:1.

MeLi/Me$_2$Mg compositions in solution in limited THF/Toluene containing 50 or more mole % Me$_2$Mg are stable and need not be refrigerated. Compositions in toluene containing less than 50 mole % Me$_2$Mg are more stable than MeLi alone, however they will require refrigeration to avoid thermal degradation. At higher temperatures degradation occurs via metallation of toluene to form benzyllithium and methane gas. MeLi/Me$_2$Mg compositions prepared in cumene are even further improved as shown by the fact that solutions of MeLi with as little as 5 mole percent Me$_2$Mg show no decomposition after storage at 40° C. for a 30 day period.

The process of this invention employs an alkali metal, preferably lithium, sodium or potassium. When preparing bimetallic compounds a mixture of two metals are employed. One metal is an alkali metal, preferably lithium and the other metal is selected from metals listed in group 2A of the Periodic Chart of Elements, aluminum and zinc preferably magnesium. The organic halide, which is typically selected from lower alkyl halides and aromatic halides, such as methyl or ethyl chloride is reacted with the mixed metals in a hydrocarbon solvent containing a limited amount of tetrahydrofuran, other ethereal compound or appropriate Lewis Base. The hydrocarbon solvent may be a liquid, lower aliphatic hydrocarbon solvent containing five to ten carbon atoms, an alicyclic hydrocarbon of six to ten carbon atoms or an aromatic hydrocarbon, preferably cumene and a limited amount of tetrahydrofuran.

The usual synthesis of the bimetallic compositions involves the slow addition, generally over one to two hours, of an organic chloride such as methyl chloride to a mixture of finely divided lithium particles and magnesium powder slurried in a hydrocarbon reaction medium containing a limited amount of tetrahydrofuran. In typical examples varying amounts of these metals are used and the reaction directly produces the desired soluble MeLi/Me$_2$Mg composition from which by-product lithium chloride and excess metals are separated by filtration. Characterization of the products was done by titrimetric, nuclear magnetic resonance and atomic absorption spectroscopy methods.

The reactivity of the finely divided lithium in producing mono-metallic or bimetallic compositions is increased by the presence of a small amount of sodium. H. O. House and M. Call in Organic Synthesis (1972), 52, 39 showed that a minimum 0.7 wt % preferably 1 to 2 weight percent sodium in the finely divided lithium is necessary for efficient and complete reaction with methyl chloride in diethyl ether.

The general procedure of the bimetallic process aspect of this invention is further described with respect to the reaction of the methyl chloride with lithium and magnesium metals in cumene containing limited amounts of tetrahydrofuran. MeLi/Me$_2$Mg of various compositions are predictably synthesized via the simultaneous reaction of methyl chloride with a mixture of washed lithium metal particles (minimum 0.7% Na) and magnesium powder slurried in toluene containing slightly more than one equivalent of tetrahydrofuran per equivalent of methyl chloride employed.

In one aspect of this invention lithium and magnesium metals are reacted with an alkyl halide such as methyl, ethyl, or butyl chloride or an aromatic halide such as phenyl chloride. Surprisingly when the reactant ratios are selected so as to provide at least 1 mole percent and preferably 5 to 10 mole percent of magnesium per mole of lithium and the alkylhalide is methylchloride a highly stable methyllithium/dimethylmagnesium solution is produced. Likewise, the reactant metal ratios can be chosen such that product ratios of alkyllithium to dialkylmagnesium may vary from 0.01 to 0.99. This aspect of this invention may be illustrated by the following equation:

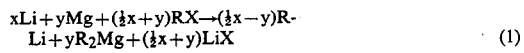
$$xLi + yMg + (\tfrac{1}{2}x+y)RX \rightarrow (\tfrac{1}{2}x-y)R\text{-}Li + yR_2Mg + (\tfrac{1}{2}x+y)LiX \qquad (1)$$

wherein x > 2 and y = 1; R is a lower alkyl or aromatic group and X is a halide.

When x=2 and y=1 in the above equation the product will be a dialkylmagnesium only. The reaction is conducted in an aliphatic hydrocarbon of five to ten carbon atoms or an aromatic hydrocarbon, containing in all cases a limited amount of tetrahydrofuran or other Lewis Base.

Dialkylmagnesium/alkylmagnesium halides of various compositions are synthesized via the process of this invention. This aspect of this invention can be represented by the following equation:

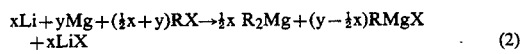
$$xLi + yMg + (\tfrac{1}{2}x+y)RX \rightarrow \tfrac{1}{2}x\,R_2Mg + (y-\tfrac{1}{2}x)RMgX + xLiX \qquad (2)$$

wherein R is lower alkyl such as methyl (Me), x is less than 2 and y is 1, and X is selected from chlorine, bromine and iodine.

Following the general procedure of the invention the two metals are slurried in an aromatic solvent, preferably cumene and the metals preconditioned (activated) by contact (stirring) with a small amount of a methylmetallic (1 to 3 mole percent based on methyl chloride used) such as MeLi, Me$_2$Mg, MeLi/Me$_2$Mg or Me$_2$Mg/MeMgCl or the like for 2 to 4 hours. Generally, for predictability not more than 20 mole % excess metals (M=Li+Mg=20% excess) should be used (based on methyl chloride), and desired MeLi/Me$_2$Mg compositions can be prepared by simply varying the relative amounts of metals employed (see equation 1 above). Dry THF is added just prior to starting the reaction. After initiation with a small amount of gaseous methyl chloride, the remaining methyl chloride is slowly added to the metal slurry over 1 to 2 hours while maintaining the reaction temperature between about 30° C. and about 50° C. but preferably between 30° C. and 40° C. generally at about 35° C. Generally, one to two hours post reaction time, with agitation assures reaction of all the methyl chloride. After the reaction, the mass is stirred until no methyl chloride is present in solution (based on NMR analysis). The reaction product is filtered to remove solids and a light yellow to water white solution of MeLi/Me$_2$Mg is recovered. The product is assayed by the methods disclosed herein.

The process of this invention for producing bimetallic compositions can be operated at temperatures from ambient up to about 50° C., but preferably 30° C. to 40° C. The reactants participate in exothermic reactions and while a reaction may initiate at ambient temperature the resultant temperature can go up to as high as 30° to 35° C. or even higher. While high temperatures are possible it is preferred to operate in the temperature range of ambient to 50° C. and typically with methyl chloride, lithium and magnesium the temperature is maintained at 30° to 35° C. While pressure reactions are possible, it is preferred to run the reaction at atmospheric pressure. The reactions should be carried out under an inert gas, preferably argon. Materials of construction of the reactors and condensors are not critical so long as they are inert to the reaction. Glass lined, stainless steel, Hastelloy, carbon steel and other quality materials of construction are suitable.

The following examples further illustrate the invention. Unless indicated otherwise temperatures are in degrees C, percentages of reactants are in weight percent. All glassware was baked in an oven (150° C.) overnight, assembled, and purged until cool with argon. An inert argon atmosphere was maintained throughout reaction, filtration, and packaging. The MeLi/Me$_2$Mg concentration and compositions were determined by Total Base, Carbon metal bond assay (W.E. titration and/or NMR), and Magnesium titration. The lithium and magnesium ratio can be confirmed by Atomic Absorption Spectroscopy. The chloride content of solution was determined by Mohr titration. All lithium metal used contained 0.7% to 1.25% sodium. The analytical data in some examples reports values for "MeM" wherein M represents a mixture of magnesium and lithium metals and Me represents methyl.

A - ALKALI METAL EXAMPLES

The first series of examples prepared methyllithium by reacting methyl iodide with n-butyllithium. The methyllithium so produced was used for solubility and stability studies. The procedure in all such examples was substantially the same except that different solvent solutions were employed. The following Experiment 2 is exemplary of the various experiments conducted:

Methyl iodide (0.1 mole) and hexane (50 ml) were added by syringe via a rubber septum to a reaction flask. The flask and contents were cooled to −20° C. with a cooling bath. n-Butyllithium (0.1 mole) was then added, also by syringe, dropwise over a period of 30 minutes while maintaining the reaction between −40 and 0° C. A white precipitate immediately formed and increased in amount throughout the reaction. The resultant slurry was stirred an additional hour to ensure the completeness of reaction. The white slurry was then transferred to the filter funnel. A rapid filtration (15 minutes) resulted in solid methyllithium (MeLi) being collected on the filter plate. The solid MeLi was then washed with 50 ml hexane and 50 ml toluene to remove impurities. The filtrate (hexane, toluene, and n-butyliodide) were removed by syringe, and a premixture of 14.7 ml tetrahydrofuran (THF) and 33.8 ml toluene was added to the filter funnel. Stirring the contents of the filtration funnel resulted in complete dissolution of the MeLi. A light yellow clear solution of MeLi was obtained by filtration (88.4% recovered yield).

| Analyses: | |
|---|---|
| Total base | = 1.50 M |
| Watson Eastham Titration | = 1.47 M |
| NMR analysis | = 1.40 M |
| | = 2.23 THF/MeLi mole ratio |

Data from additional examples preparing methyllithium by the method of Experiment 2 are contained in Table 1.

The data in the tables was obtained by two titration methods and proton NMR. The total base (alkalinity/content) titration determines the equivalents of water soluble basic lithium hydroxide which forms when a methyllithium sample is hydrolyzed.

The active lithium was determined by a modified Watson-Eastham method (Watson, S. C.; Eastham, J. F.; J. Organomet. Chem. (1967), 9, 165). This method not only titrates methyllithium but also any other strongly basic species such as metallated THF or toluene which may be contained in thermally degraded samples.

Proton (NMR) analysis was used for assaying methyllithium samples regardless of the extent of the amount of decomposition. The modified Watson-Eastham titration did not distinguish between methyllithium and any other carbon lithium species present in a decomposed sample. Visually, decomposed samples were readily identified by their dark red color. Non-degraded samples were a light yellow color. The Watson-Eastham and NMR analyses were in excellent agreement for freshly prepared, non-degraded methyllithium samples.

In one experiment (see Table I - Exp. No. 1), an attempt to dissolve solid methyllithium with one equivalent of THF in toluene resulted in initial solubility; however, a precipitate formed overnight. Filtration resulted in about 50% of the total methyllithium being soluble (0.60M) and the soluble product being composed of a 2.08 THF:MeLi complex. The remaining MeLi was dissolved with additional THF/toluene solution in order to determine yield (76.6%). In another experiment (see Table I - Exp. No. 2), essentially all the solid methyllithium was dissolved in a solution of toluene containing two equivalents of THF (MeLi=1.40M - yield 88.4% -THF/MeLi by NMR - 2.23 mole ratio). This solution remained clear (no pptn.) after 47 days in the refrigerator (0° to 6° C.) indicating good solution stability in cold weather. The above MeLi solutions were subjected to thermal stability testing at 0° C. and room temperature.

In a further experiment (see Table I - Exp. No. 3), an attempt to dissolve solid methyllithium with cyclohexane containing two equivalents of THF resulted in a sparingly soluble product (MeLi=0.20M - THF/MeLi=18.5 mole ratio) which precipitated (clear solution=0.13M) overnight in the refrigerator at 0° C. In the final experiment (see Table I - Exp. No. 4) an attempt to dissolve solid methyllithium with toluene containing two equivalents of diethyl ether (Et$_2$O) also resulted in a slightly soluble product. (MeLi=0.14M - THF/MeLi=22.2 mole ratio.)

The process of preparing methyllithium exemplified in Experiment 2 and detailed in Table I while suitable for laboratory investigations does not appear to be a suitable commercial process because of the cost of nbutyllithium and methyl iodide. The present invention provides a method of preparing methyllithium from lithium metal, preferably a finely divided lithium metal dispersion, containing from a trace to 2 weight % sodium and a methyl halide in a THF/aromatic hydrocarbon solvent such as toluene.

The general method of this aspect of the invention was to use an argon atmosphere and feed gaseous methyl chloride slowly over one to two hours into a slurry of lithium metal dispersed in an aromatic hydrocarbon/THF medium maintained at 30° to 35° C. Rapid addition of methyl chloride (MeCl) can result in coupling (MeLi+MeCl→Ethane+LiCl) which reduces yield. Also, limiting the THF at the start of reaction and adding the THF incrementally throughout the reaction apparently prevents cleavage of the ether and coupling, resulting in a higher recovered yield. Before filtration the reaction mass was stirred overnight to ensure complete reaction and thus limit occurrence of post-reaction coupling (PRC) after filtration. As noted above, PRC lowers yield and results in ethane gas pressure and a hazy (cloudy) MeLi solution due to the resultant very fine lithium chloride precipitate. Filtration yielded a light yellow solution of MeLi:THF in toluene. The MeLi content of solution was determined by total base and active carbon-lithium analysis and the mole ratio of THF/MeLi by proton NMR. Solutions of methyllithium containing two or less equivalents of THF were found to be stable at room temperature (16° to 22° C.) for at least 30 days and indefinitely stable under mild refrigeration (0° to 6° C.). At higher temperatures degradation occurs via metallation of toluene to form benzyllithium and methane. The analytical methods are discussed above. The lithium metal used throughout these examples, unless noted otherwise, was a dispersion containing 18.2 weight percent finely divided lithium metal (containing 1.36 weight % sodium based on lithium content) dispersed in mineral oil.

A second series of examples (5 to 11) prepared methyllithium by reacting methyl chloride with lithium dispersion under an argon atmosphere. The following Example 10 (Table II) is exemplary of this series of experiments: Lithium dispersion (59.4 g) was prewashed in a filter funnel with 100 ml toluene. The wash toluene and oil was removed by filtration and the lithium dispersion slurried with 250 ml toluene. The slurry was transferred to the reaction flask along with 5 ml MeLi in limited THF/toluene (1.55M). The resultant mixture was stirred for 30 minutes in order to condition the surface (increase reactivity) of the lithium particles. Tetrahydrofuran (0.56 moles) was added to the contents of the flask prior to reaction with methyl chloride. An additional 0.28 moles of THF was added after 67% of the methyl chloride had been added. The reaction was initiated by the addition of 1.5 g MeCl. The temperature rose from 22° to 35° C. in eight minutes indicating a rapid initiation. The remaining MeCl (31.5 g) was slowly added over a period of one hour and 50 minutes, while maintaining the reaction temperature between 30° and 35° C. The reaction mass was allowed to slowly stir overnight. Filtration resulted in a light yellow solution of MeLi (recovered yield=87.5% based on MeCl used).

Analyses:  Total Base = 1.55 M; Active Lithium (W.E. Titration) = 1.55 M; NMR Analysis = 1.65 M and 1.36 mole ratio THF/MeLi.

The first experiment in this series (see Table II, Exp. No. 5), used an extruded lithium rod (0.7% Na) cut into small ¼" pieces and slurried with toluene/THF which, when contacted with gaseous MeCl, resulted in a very slow reaction and low yield (34.7%).

Reactivity was increased by using finely divided lithium dispersion containing 1.36 wt. % sodium; this dispersion was used for the next six experiments (see Exp. 6-11, Table II for details). In another experiment (see Table II, Exp. No. 6), gaseous MeCl was fed to a lithium dispersion slurry in THF/toluene for one hour. The reaction produced a slightly yellow solution of MeLi (1.59M or 4.0 wt. %) in an excellent 87.2% recovered yield. NMR analysis verified the yield and indicated the product to have a 1.73 THF:MeLi mole ratio. The next five experiments involved preliminary reaction variable studies necessary for ascertaining the most efficient way to synthesize MeLi while maintaining a quality product, solubility, and high yields. The most critical yield reducing variable was determined to be the amount of THF present during the reaction (expressed in Table II as THF/MeCl mole ratio). When this mole ratio increased beyond about 1.5, yields of MeLi dropped drastically and gassing occurred indicating Wurtz coupling.

Additional experiments were conducted using various THF/MeCl mole ratios to further study the effect of the THF/MeCl ratio of methyllithium yield. Data from these additional examples, together with selected data from Table II and from the literature are set forth in Table IX. These data show maximum yield occurs when the Lewis Base (THF) is limited to 1.1 to 1.42 moles of Lewis Base per mole of MeCl. Examples 8 and 9 illustrate the detrimental effect of too much THF. Gilman, even at 0° C., got low yields (see Table IX) when reacting methylchloride and lithium in THF solvent alone.

Experiment 6 was repeated substituting gaseous methyl bromide for methyl chloride (see Table II, Example 12). The reaction of methyl bromide with lithium dispersion in toluene containing a limited amount of THF (THF/MeBr=1.22 mole ratio), unexpectedly resulted in the formation of a highly soluble $MeLi_{1.0}$·$LiBr_{0.69}$ complex. After filtration, the solution contained 1.43 moles MeLi and 0.99 moles of LiBr per liter of solution. Thus, utilizing the process of this invention a soluble MeLi.LiBr complex was synthesized even though the THF content in the reaction was limited. This sample was subjected to thermal stability testing and was found to be significantly more stable than "halide-free" methyllithium solutions in limited THF/toluene.

THERMAL STABILITY

The thermal stability of the methyllithium complexed with various amounts of THF and dissolved in toluene was investigated. The thermal stability of the complexes was monitored by NMR analyses. The modified Watson-Eastham method gave erroneous results on degraded samples but closely agreed with the NMR analyses of non-degraded samples. The thermal stability data in Tables III and IV illustrate the stability of MeLi solutions containing 2 equivalents and 4 equivalents of THF per equivalent of methyllithium in toluene of samples stored at room temperature over a number of days.

Atmospheric contamination was likely due to the repetitive sampling of a single container of each solution (Method A). Clearly, limiting the amount of THF has a profound effect on the thermal stability of methyllithium/THF complexes in solution in toluene.

Additional thermal stability studies were conducted using multiple sample bottles which were sampled once and discarded (Method B). Samples containing various amounts of THF were prepared according to the procedure of Experiment 6, tested at 40° C., room temperature and 0° C., and assayed by NMR at various times for methyllithium content (loss). A MeLi:4.26 THF complex degraded very rapidly at 40° C. and at room temperature (see Table VI) losing 93.7 and 71.9% activity after six and 27 days, respectively. The solutions turned dark red, contained high methane gas pressure, but contained no precipitation, all of which are indicative of toluene metallation. After 28 days at 0° C., the MeLi:4.26 THF was relatively stable showing 4% loss. However, the color of the solution did change from light yellow to orange-yellow, but was clear, again indicating slight metallation.

Samples of a MeLi:3.06 THF complex in toluene respectively lost 95 and 35% MeLi after eleven days at 40° C. and 26 days at room temperature (see Table V). The solutions both turned dark red (metallation), contained methane gas, but no precipitate. After 27 days at 0° C., NMR indicated no loss of MeLi. However, the MeLi:3.06 THF solution had turned orange, contained slight methane gas pressure which may indicate a slight amount of decomposition.

Reducing the amount of THF resulted in even slower decomposition (metallation). After 27 days at 40° C., a MeLi:1.36 THF solution in toluene lost 64.5% MeLi (see Table VII). This solution also turned dark red, contained no precipitate, but heavy methane gas pressure. At room temperature the MeLi:1.36 THF solution remained yellow (no pptn.), contained slight methane gas pressure, and lost only 5.7% methyllithium after 27 days. After 27 days at 0° C. this solution (MeLi:1.36 THF) exhibited no loss of MeLi, contained no gas, and remained yellow (see Table VII). The thermal stability data of methyllithium in various Lewis bases and co-solvents and the $MeLi_{1.0}LiBr_{0.69}$ complex in limited THF/toluene are summarized in Table XI.

The data presented in Table XI demonstrates that "halide-free" methyllithium solutions in toluene are significantly more thermally stable if the THF content is limited to 2 or less moles of THF per mole of methyllithium in solution, preferably 1.2 to 1.5 moles of THF per mole MeLi. (See Experiments 1-A, 1-B, 8, 9 and 10.) Also, in limited THF/toluene, a methyllithium solution containing 0.69 molar equivalents of lithium bromide ($MeLi_{1.0}LiBr_{0.69}$ complex) was, unexpectedly found to be about eight times more stable than the "halide-free" methyllithium examples shown in Table XI. (See Example 12.) Table XI also shows that methyllithium dissolved n limited THF (THF/MeLi=1.3 to 1.8 mole ratio) and in aromatic solvents having fewer metallable hydrogens than toluene also results in improved thermal stability. Substituting benzene, cumene or ethylbenzene for toluene resulted in improved thermal stability which was about 8, 5 and 3 times, respectively, more stable over the comparable methyllithium solutions in limited THF/toluene (see Table XI, Examples Nos. 20, 13, 14 and 10). Thus, by restricting the THF content of the solution to 2 or less equivalents of THF, or other Lewis Base, per mole of dissolved methyllithium, selecting a less metallable aromatic solvent or incorporating lithium bromide as stabilizer has resulted in commercially viable methyllithium compositions which can be efficiently synthesized according to the process of this invention.

SOLUBILITY

Solution stability testing (or product solubility) was done to determine the resistance to product precipitation due to cold weather. Samples of varying methyllithium concentration containing varying amounts of THF were placed in a refrigerator at 3 ± 3° C. and visually monitored for product precipitation with time (see Table VIII). All samples tested remained in solution indicating good solution stability including the MeLi sample containing the least amount of THF. (See Table VIII, Experiment No. 10).

MeLi was found to have virtually no solubility in hydrocarbon solvents (Table X, Exps. 2-A in toluene and 2-B in n-hexane). The solubility of MeLi in THF alone was not determined because this composition has no commercial value in terms of storage and shipping due to thermal instability (cleavage). Attempts to prepare MeLi in limited diethylether/toluene (Table X, Exp. No. 4), in limited triethylamine (TEA)/toluene (Exp. No. 19-A) and in TEA alone (Exp. No. 19-B) resulted in quite insoluble products. MeLi was also found virtually insoluble in limited t-butylmethylether/toluene (Exp. No. 21-A) and in t-butylmethylether alone (Exp. No. 21-B). In limited dimethylether/toluene (Exp. No. 22) MeLi was initially soluble (Total Base=0.87M), but partially precipitated overnight (Total Base=0.42M of the clear supernatant solution) as the dietherate. These results virtually eliminate the possibility of achieving solubility in longer chain, less polar dialkylethers or tertiary amines.

The necessity for an aromatic solvent in combination with a limited amount of THF for reasonable solubility was demonstrated in Experiment 3 (Table X). Substituting cyclohexane for toluene yields a highly insoluble MeLi complex. Also, employing a mixed aromatic/cyclic hydrocarbon co-solvent (toluene=2.0 eq/MeLi and cyclohexane =3.0 eq/MeLi) in combination with a limited amount of THF also resulted in low solubility (0.46M Exp. No. 15). These data strongly indicate that a strong Lewis Base, such as THF, and an aromatic solvent, such as toluene, provide a novel solvent composition for MeLi.

Table X also presents solubility data for MeLi in limited THF or 2-methyltetrahydrofuran (MTHF) and other aromatic solvents. Methylchloride and lithium dispersion were employed for these preps and solubilities were purposely exceeded in order to establish limits. In each synthesis more than 7% of the total MeLi formed was left on the filter plate, verifying that the solubility limit was approached. The best solvent combination found for MeLi was limited THF and benzene (Table X, Exp. No. 20) even exceeding the solubility limit of "halide free" MeLi in diethylether alone by about 10%. In substituted aromatic solvents containing limited THF solubility limits decreased according to the size of aliphatic hydrocarbon substituent attached to the benzene ring (benzene > toluene > ethylbenzene > isopropylbenzene > t-butylbenzene). In terms of solubility benzene (Exp. No. 20) and toluene (Exp. No. 10) were determined to be the best aromatic co-solvents for MeLi. Ethylbenzene (Exp. No. 13) and isopropylbenzene (Exp. No. 14) were also acceptable co-solvents for MeLi. t-Butylbenzene (Exp. No. 16) was deemed unacceptable, not only because of low solubility (0.86M), but also because in combination with limited THF a metastable solution was formed which precipitated MeLi when subjected to either cold or hot temperatures.

In Table X, Exp. Nos. 17 and 18, demonstrated that a soluble MeLi composition can be generated from methylchloride and lithium in aromatic solvents and a limited amount of Lewis Base similar to, but other than, THF. The fact that 2-methyltetrahydrofuran (MTHF) was alkyl substituted and, thus, slightly less polar than THF was reflected in the solubility data. In limited MTHF/toluene MeLi was determined acceptably soluble (1.37M). MeLi in limited MTHF/isopropylbenzene was found to be not only marginally soluble (1.01M) but also metastable in terms of product precipitation.

The above data stress the necessity of an aromatic or substituted aromatic co-solvent to generate a soluble MeLi:limited THF complex. Other Lewis bases similar to THF (MTHF) also solvate, but weaker Lewis bases (Et$_2$O, TEA, DME, TBME, etc.) in limited amounts with aromatic co-solvents were not effective. Solubility data are summarized in Table X.

B - BIMETALLIC EXAMPLES

Synthesis of Methyllithium/Dimethylmagnesium Compositions

EXAMPLE 23

Lithium dispersion (2.8 moles of Li dispersed in mineral oil) was pre-washed in a filter funnel with 300 ml toluene. The toluene wash and oil were removed by filtration, and the lithium was re-slurried with 400 ml of fresh toluene. The slurry was transferred to a 500 ml reaction flask along with 40 ml of MeLi solution. Magnesium powder (0.18 moles) was then added using 50 ml of toluene to rinse the weighing vessel. This mixture was stirred for 4.5 hours in order to precondition (increase reactivity) of the metals. THF (99 ml) was then added. The reaction was initiated by the addition of 1.5 g of gaseous MeCl. The temperature rose from 21 to 33° C. in about four minutes. The remaining MeCl (65.7 g) was fed continuously over a period of two hours while maintaining the reaction mass temperature between 30 and 35° C. After one hour the stirring was stopped and the reaction mass allowed to settle. NMR analysis of a clear decanted sample indicated no residual MeCl. Filtration yielded 545 ml of a clear, light yellow solution of MeLi/Me$_2$Mg (78.4% yield - 1st filtration). Two washes of the filter cake with toluene (100 ml) and THF (100 ml) increased the overall yield to 91%.

The composition of the MeLi/Me$_2$Mg product in solution was 86/14 mole percent.

EXAMPLES 24–31

Example 23 was repeated a number of times to produce various ratios of MeLi to Me2Mg in toluene or in cumene. The preparative and analytical results of Examples 23 through 31 are reported in Table XII.

Synthesis of Dimethylmagnesium

EXAMPLES 32 and 33

Lithium dispersion (0.78 moles dispersed in mineral oil) was washed in a filter funnel twice with ~100 ml of toluene. The toluene wash and oil were removed by filtration, and then the fine lithium particles were slurried with 190 ml of toluene. The slurry was transferred to a one liter reaction flask along with 17 ml of methyllithium in THF/cumene (0.02 moles). Next, magnesium metal powder (0.39 moles) was added to the contents of the flask. Residual magnesium on the weighing vessel was washed in with 28 ml of toluene. The resultant slurry was then stirred for four hours in order to condition (activate) the metals for reaction.

Next, THF (0.81 moles) was added and the reaction initiated by the addition of 1 gram of MeCl. The temperature rose from 20° C. to 31° C. in two minutes, indicating rapid initiation. The remaining MeCl (35 g) was added as a gas over a period of 67 minutes. The reaction temperature was controlled (30° to 40° C.) by means of a cooling bath. The reaction temperature began to drop immediately after the halide addition. Stirring of the reaction mass was continued overnight. NMR analysis of a clear sample taken the next morning indicated no residual MeCl. Filtration yielded 276 ml of a clear, water white, non-viscous clear solution of dimethylmagnesium.

Example 32 was repeated to produce a saturated solution of dimethylmagnesium in toluene and labeled Example 33. The preparative and analytical details of Examples 32 and 33 are shown in Table XIII and the thermal stability results of Example 33 in Table XVII.

Synthesis of Me$_2$Mg/MeMgCl Compositions

EXAMPLES 34 and 35

Lithium dispersion (0.52 mole dispersed in mineral oil) was prewashed (twice) in a filter funnel with 100 ml aliquots of toluene. The toluene and oil were removed by filtration, and the lithium reslurried in toluene (190 ml). The lithium slurry was transferred to a one liter reaction flask. Then, magnesium (0.52 mole) and the metal conditioner (0.01 mole Me$_2$Mg in toluene) were added. This mixture was stirred (four hours) in order to condition (activate) the metals prior to initiation. Next, THF (0.84 moles) was added, and the reaction initiated with MeCl (~1 g). The temperature rose from 26° to 39° C. in about four minutes indicating a rapid initiation. The remaining MeCl (34.6 g) was fed continuously over a period of 70 minutes while maintaining the reaction temperature at ~35° C. The reaction mixture was allowed to stir overnight. Filtration was slow (~ five hours), yielding a clear light yellow solution. Only 179 ml of product solution (60.2% yield) was obtained, indicating insoluble product and/or incomplete filtration. A THF wash (100 ml) resulted in recovery of additional product (83.9% total yield). This experiment was repeated and given number 35. The preparative and analytical details for Examples 34 and 35 are contained in Table XIV.

Synthesis of Me$_2$Mg/MeLi (85/15 mole %) in Cyclohexane Containing a Limited Amount of THF

EXAMPLE 36

The Me$_2$Mg/MeLi (85/15 mole %) is synthesized from the direct reaction of gaseous methylchloride with a mixture of lithium dispersion and magnesium powder slurried in toluene containing a limited amount of THF. The synthesis as represented by Equation 1 (where x=2, y=) was intended to generate dimethylmagnesium (no MeLi) but actually resulted in a Me$_2$Mg/MeLi composition (85/15 mole %), possibly because of solvent effects.

Lithium dispersion (1.17 mole) was washed twice in a filter funnel with 100 ml aliquots of cyclohexane. The toluene wash and oil were removed by filtration. The lithium was reslurried in cyclohexane (260 ml) and then transferred to the reaction assembly. Next, magnesium powder (0.59 moles) and MeLi (0.03 moles) were charged. The resultant slurry was allowed to stir (7.5 hours) in order to condition (activate) the metals. Next, THF (100 ml) and then MeCl (1 g) were added to the contents of the flask. A rapid rise in temperature (9° C. in three minutes) indicated efficient initiation. The remaining MeCl (52.8 g) was added slowly as a gas over a period of ~2 hours while maintaining the reaction temperature at 32° C. ± 3° C. The reaction mass was slowly stirred overnight. Filtration resulted in two phases, a clear upper layer and a gold-brown lower layer. NMR analysis revealed the following product/solvent distribution: Upper Layer=0.86 N (Me), Me:THF:Cyclohexane=1:2.1:10 mole ratio; Lower Layer=5.9 N (Me), Me: THF:Cyclohexane =1:0.96:0.65 mole ratio. The muds in the filter funnel were washed with two 50 ml aliquots of THF and filtered directly onto the two layers remaining in the receiving flask. The resultant two layer system was stirred for 1.5 hours and then was again allowed to form two layers which were separated and bottled (Upper Layer =276.2 g; Lower Layer=81.6 g). Each layer was then analyzed. The results follow: Upper Layer- Total Base =b 1.78N; W.E. Titration=1.90N; Mg Titration=0.80M NMR - 1.81 in active MeM 2.0 THF/Active MeM (mole ratio) A.A. Analysis - 0.20M Li, 0.77M Mg; Cl Titration=0.06M; Density=0.812 g/cc; yield - 56.6 (upper layer only); composition - Me2Mg/MeLi (85/15 mole %). Lower Layer - Total Base=3.03N; W.E. Titration=3.01N; Mg Titration - 1.32N; NMR=3.25N in Active MeM, 1.57 THF/Active MeM (mole ratio); A.A. Analysis=0.37M Li and 1.32M Mg; Cl Titration=0.10M; Density=0.834 g/cc Yield=27.7% (lower layer only). Composition Me2Mg/MeLi=83/17 (mole/mole).

The total recovered yield (both layers) was 84.3% (based on moles MeCl used) of Me2Mg/MeLi. Both layers have the same Mg/Li mole ratio. On cooling to 0° C., both of the separate one phase layers (at room temp.) again formed two distinct layers with the denser phases being highly concentrated in MeM. The addition of more THF immediately resulted in a single phase system (1.45 N in active Me; Me:THF:Cyclohexane=1:3.3:3.6) which remained a single phase upon prolonged cooling at 0° C. This indicates that at least 3 equivalents of THF are required per methyl group if the solvent is non-aromatic.

Synthesis of Ethyllithium/Diethylmagnesium (93/7 mole %) in Cyclohexane Containing a Limited Amount of THF

EXAMPLE 37

Lithium, (1.28 moles dispersed in mineral oil), was washed with two 200 ml aliquots of cyclohexane. Cyclohexane, containing the mineral oil, was removed by syringe after allowing the lithium to rise to the top of the solution. Next, magnesium powder (0.032 moles), cyclohexane (293 ml), and n-butyllithium (0.005 moles) were charged to the reaction flask. The contents of the flask were stirred overnight in order to condition (activate) the metals. Next, 25 ml dry THF was added to the flask. The reaction was initiated by the addition of two 1 g and one 1.5 g charges of ethylchloride as evidenced by a gradual rise in temperature (24° to 35° C. in 40 minutes). The remaining ethylchloride was added over a period of 118 minutes. The reaction temperature was controlled between 30° and 35° C. by means of the Dryice/hexane cooling bath. An NMR of clear decanted product solution taken after 65 minutes of post reaction time indicated 1.10 N solution of Ethyl-M containing some unreacted ethylchloride (0.16 M). The reaction mass was stirred overnight. Filtration yielded 293 ml of a clear, light yellow solution. The analytical results appear below.

| Analytical Results (First Filtration) | |
|---|---|
| Total Base | = 1.27 N |
| Mg Titration | = 0.079 M |
| NMR | = 1.30 N Active ethyl group |
| | = 0.675 THF/Active ethyl group (mole ratio) |
| A.A. Analysis | = 0.96 M Li |
| | = 0.08 M Mg |
| Cl Titration | = 0.055 M |
| Density | = 0.778 g/cc |
| Recovery Yield | = 79.0% |
| Composition | = Ethyllithium/diethylmagnesium (93.4/6.6 mole %) |

The filtration muds were washed with a mixture of THF (7 ml) and cyclohexane (93 ml) yielding 100 ml of a yellow solution (Total Base 0.63 N, Mg=0.044 M). Both product solutions were refrigerated.

Synthesis of Me2Mg/MeNa Via The Reduction of Me2Mg With Na Metal in Toluene Containing a Limited Amount of THF

EXAMPLE 38

Although the method of preparation shown in this example is not covered under Equations 1 and 2 above, this example is described to show variation of the composition from lithium to sodium.

Dimethylmagnesium prepared according to Example 32 in limited THF/toluene (0.055 moles) was added by syringe to a pre-dried, argon purged bottle (125 ml) which was fitted with a rubber septum and contained a magnetic stirring bar. Next, freshly prepared finely divided sodium dispersion (8.6 g) suspended in toluene (39 ml) was syringed into the bottle. The mass was swirled and a dark grey-black precipitate began to form immediately. The mixture was slowly stirred overnight. The insoluble mass had become lighter (greyish) during this time. Stirring was stopped allowing the insoluble material to settle to the bottom of the bottle. About 38 ml of the almost clear supernate was removed by syringe and analyzed (after centrifugation). The analytical results follow:

| | |
|---|---|
| Total Base | = 0.80 N |
| Mg Titration | = 0.26 M |
| A.A. Analysis | = 0.27 M Magnesium |
| | = 0.20 M Sodium |
| NMR Analysis | = 0.75 N (Active methyl group) |
| | = 3.12 Mole ratio THF/Me |
| Composition | = Me2Mg/MeNa = 57/43 mole % |

THF (20 ml) was then added to the bottle containing the precipitate and remaining solution. The mixture was stirred and then filtered prior to analysis. The analytical results follow:

| | |
|---|---|
| A.A. Analysis | = 0.50 M Sodium |
| | = 0.50 M Magnesium |
| NMR Analysis | = 1.66 N in Active methyl group |

-continued

| Composition | = 3.64 Mole ratio THF/Me = Me$_2$Mg/MeNa = 50/50 mole % |
|---|---|

The total recovered yield (based on active methyl group) including solution removed for analyses was 92%.

Thermal Stability and Solubility Studies

The thermal stability of a number of examples shown in Table XII were determined by dividing the product in each example into six sample bottles which were stored at the temperature and for the time periods set forth in Table XV.

Examples 24 and 25 in Table XV show that MeLi/Me$_2$Mg compositions in toluene containing at least 50 mole % Me$_2$Mg are stable indefinitely even at elevated temperatures. Examples 23 and 28 of Table XV in toluene containing lesser amounts of Me$_2$Mg are significantly more stable than MeLi alone (Example 10). By substituting cumene as solvent for toluene (Example 29) only small amounts of Me$_2$Mg (5 to 10 mole %) were necessary to obtain equivalent stability to toluene solutions containing at least 50 mole % Me$_2$Mg (Examples 24 and 25).

Table XVI shows a comparison of the solubility of MeLi alone, and MeLi/Me$_2$Mg compositions in aromatic solvents at various temperatures. Incorporation of small amounts of Me$_2$Mg (4–14 mole %) (Examples 23, 29, 30, 31) in the MeLi solution increased the solubility of the MeLi at all temperatures tested.

These solubility and thermal stability studies show that even small amounts of a dialkylmagnesium will enhance the thermal stability of the corresponding alkyllithium in a hydrocarbon solvent containing a limited amount of THF.

Dimethylmagnesium alone shows no loss of thermal stability under all testing conditions (see Table XVII).

TABLE I

Preparation of Methyllithium from Methyliodide and n-Butyllithium in Various Solvents

| | Reagents | | | | | | | NMR Analysis | | |
|---|---|---|---|---|---|---|---|---|---|---|
| Ex. No. | Methyl Iodide (moles) | n-Butyl-lithium (moles) | Ether (moles) | Solvent (ml) | Reaction Temp. (°C.) | Conc. (Theory) (M.) | Conc. Found[1] (M.) | Recovered Yield (%) | Conc. (M) | THF/MeLi (Mole Ratio) | Remarks |
| 1 | 0.1 | 0.1 | 0.1 THF | 62 Toluene | 0 to 10 | 1.55 | 0.60 | 76.6 | 0.60 | 2.08 | One THF dissolved only 50% of the MeLi formed. |
| 2 | 0.1 | 0.1 | 0.2 THF | 34 Toluene | −40 to 0 | 1.50 | 1.47 | 88.4 | 1.40 | 2.23 | Two THF dissolved all MeLi formed |
| 3 | 0.1 | 0.1 | 0.2 THF | 85 Cyclo-Hexane | −40 to 0 | 0.93 | 0.24 | 89.8 | 0.20 | 18.46 | 50% of the dissolved MeLi precipitated overnight at 0° C. |
| 4 | 0.1 | 0.1 | 0.2 Et$_2$O | 35 Toluene | −50 to 0 | 1.54 | 0.17 | 62.82 | 0.14 | 22.20 | Two Et$_2$O dissolved only 10% of the MeLi formed |

[1]Total lithium (base) analysis.
[2]Lost product due to pumping accident which reduced yield.

TABLE II

Preparation of Methyllithium from Lithium and Methyl Halide in Toluene/THF

| | Reagents | | | | | | | | | NMR Analysis | |
|---|---|---|---|---|---|---|---|---|---|---|---|
| Ex. No. | Lithium (moles) | MeCl (moles) | THF (moles) | Li/MeCl (mole ratio) | THF/MeCl (mole ratio) | Toluene (ml) | Conc[1] Theory (M) | Total Base (M) | W.E. [2]Titration (M) | (M) | THF/MeLi (mole ratio) | Recovered Yield (%) |
| 5 | 1.09[3] | 0.50 | 0.90 | 2.18 | 1.80 | 230 | 1.58 | 0.56 | — | 0.51 | 5.24 | 34.7 |
| 6 | 0.93[4] | 0.26 | 0.37[5] | 3.58 | 1.42 | 75 | 2.20 | 1.59 | — | 1.75 | 1.73 | 87.2 |
| 7 | 1.11[4] | 0.50 | 0.78[6] | 2.22 | 1.56 | 126 | 2.41 | 1.66 | 1.75 | 1.70 | 2.15 | 75.8 |
| 8 | 1.58[4] | 0.69 | 1.24[5] | 2.29 | 1.78 | 174 | 2.31 | 1.39 | 1.50 | 1.40 | 3.05 | 60.4 |
| 9 | 1.55[4] | 0.65 | 1.23[5] | 2.38 | 1.89 | 250 | 1.74 | 0.94 | 0.98 | 0.96 | 3.49 | 50.0 |
| 10 | 1.55[4] | 0.64 | 0.84[7] | 2.40 | 1.30 | 250 | 1.88 | 1.55 | 1.55 | 1.65 | 1.36 | 87.5 |
| 11 | 1.60[4] | 0.73 | 0.66[5] | 2.19 | 0.90 | 264 | 2.0 | 1.44 | 1.41 | 1.41 | 1.34 | 71.5 |
| 12 | 1.35[4] | 0.45[8] | 0.60[5] | 2.75 | 1.22 | 161 | 1.86 | 1.43 | 1.42 | 1.49 | 1.65 | 77.0 |

[1]Calculated as 100% yield based on the amount of MeX used.
[2]Active titration as determined by the Watson-Eastham titration.
[3]Used lithium rod cut into ¼" pieces.
[4]Used lithium dispersion containing 1.36 wt. % sodium.
[5]All THF present at start of reaction.
[6]THF limited during reaction: 50% added at the start of reaction; 25% added at 50% and 75% of the halide feed.
[7]Added 67% to total THF at start of reaction and 33% of the total THF after 68% of the total MeCl was added.
[8]Employed methyl bromide instead of methyl chloride.

TABLE III

Thermal Stability[1] of MeLi:2.08 THF[2] in Toluene at Room Temperature (Ex. No. 1-A)

| Days | Temp[3] (°C.) | Loss MeLi[4] % (%/day) | Total Base[5] (M) | W.E. Titration[6] (M) | Sample Appearance |
|---|---|---|---|---|---|
| 0  | 18 ± 4 | 0      | 0.60 | —    | Light yellow clear soln |
| 6  | 18 ± 4 | 0      | —    | —    | Light yellow soln - slightly hazy |
| 12 | 18 ± 4 | 0      | —    | —    | Light yellow orange solution |
| 26 | 18 ± 4 | 0      | —    | —    | Light yellow orange solution |
| 35 | 18 ± 4 | 0      | —    | —    | Light yellow orange solution |
| 53 | 18 ± 4 | 0 (0)  | 0.64 | 0.53 | Yellow orange soln. slight pptn. |

[1]Method A. One bottle of methyllithium was sampled over and over.
[2]Solid methyllithium was prepared from n-Butyllithium and methyl iodide, dried, and then dissolved in THF/toluene (see Table I, Ex. No. 1).
[3]Sample was placed on lab bench. The laboratory temperature ranged from 14 to 22° C. in December and January.
[4]Loss of MeLi was determined by NMR.
[5]Total base = total alkalinity or total base. Determined by acid base titration after hydrolysis.
[6]Modified Watson-Eastham titration for active carbon-lithium.

TABLE IV

Thermal Stability[1] of MeLi:4.22 THF[2] in Toluene at Room Temperature (Ex. No. 1-B)

| Days | Temp[3] (°C.) | Loss MeLi[4] % (%/day) | Total Base[5] (M) | W.E. Titration[6] (M) | Sample Appearance |
|---|---|---|---|---|---|
| 0  | 18 ± 4 | 0           | 0.52 | —    | Light yellow clear solution |
| 5  | 18 ± 4 | 10.2        | —    | —    | Yellow red solution |
| 11 | 18 ± 4 | 20.4        | —    | —    | Red brown solution no pptn. |
| 25 | 18 ± 4 | 34.7        | 0.54 | 0.46 | Red brown solution no pptn. |
| 34 | 18 ± 4 | 55.1        | —    | —    | Red brown solution no pptn. |
| 52 | 18 ± 4 | 77.6 (1.49) | 0.52 | 0.40 | Red brown solution no pptn. |

[1]Method A. One bottle of methyllithium was sampled over and over.
[2]Solid methyllithium was prepared from n-Butyllithium and methyl iodide, dried, and then dissolved in THF/toluene (see Table I, Ex. No. 1).
[3]Sample was placed on lab bench. The laboratory temperature ranged from 14 to 22° C. in December and January.
[4]Loss of MeLi was determined by NMR.
[5]Total base = total alkalinity or total base. Determined by acid base titration after hydrolysis.
[6]Modified Watson-Eastham titration for active carbon-lithium.

TABLE V

Thermal Stability[1] of MeLi:3.06 THF[2] in Toluene at Various Temperatures (Ex. No. 8)

| Days | Temp (°C.) | Loss MeLi[3] % (%/day) | Total Base[4] (M) | W.E. Titration[5] (M) | Sample Appearance |
|---|---|---|---|---|---|
| 0  | —           | 0          | 1.39 | 1.50 | Light yellow solution |
| 11 | 40 ± 0.5[6] | 95 (8.63)  | 1.48 | 0.59 | Sample dark, dark red contained lost of gas - no pptn. |
| 26 | 20 ± 4[7]   | 35 (1.35)  | 1.41 | 1.27 | Sample red - contained some gas - no pptn. |
| 27 | 3 ± 3[8]    | 0 (0)      | 1.40 | 1.40 | Sample orange - contained slight gas - no pptn. |

[1]Method B. Six bottles of MeLi solution were prepared.
[2]MeLi was prepared from lithium dispersion and gaseous methyl chloride in toluene (see Table II, Ex. No. 8).
[3]Loss of methyllithium was determined by NMR.
[4]Total base = total alkalinity or total lithium. Determined by acid - base titration after hydrolysis.
[5]Modified Watson-Eastham titration for active C-Li.
[6]Methyllithium samples were placed in a constant temperature both (40 ± 0.5° C.) for the duration of the test.
[7]Methyllithium samples were placed in the laboratory for the duration of the test. The temperature in the lab ranged from 18 to 26° C. during March, 1986.
[8]Methyllithium samples were placed in the refrigerator. The temperature ranged from 0 to 6° C.

TABLE VI

Thermal Stability[1] of MeLi:4.26 THF[2] in Toluene at Various Temperatures (Ex. No. 9)

| Days | Temp (°C.) | Loss MeLi[3] % (%/day) | Total Base[4] (M) | W.E. Titration[5] (M) | Sample Appearance |
|---|---|---|---|---|---|
| 0  | —           | 0              | 0.89 | 0.95 | Light yellow solution |
| 6  | 40 ± 0.5[6] | 93.7 (15.62)   | 0.94 | 0.58 | Dark red solution - high gas pressure - no pptn. |
| 27 | 20 ± 4[7]   | 71.9 (2.67)    | 0.91 | 0.75 | Red solution - some pressure - no pptn. |
| 28 | 3 ± 3[8]    | 4.0            | 0.90 | 0.93 | Solution yellow-orange - no pptn. No gas pressure |

TABLE VI-continued

Thermal Stability[1] of MeLi:4.26 THF[2] in Toluene at Various Temperatures (Ex. No. 9)

| Days | Temp (°C.) | Loss MeLi[3] % (%/day) | Total Base[4] (M) | W.E. Titration[5] (M) | Sample Appearance |
|---|---|---|---|---|---|
| | | (0.14) | | | |

[1]Method B. Six bottles of MeLi solution were prepared.
[2]MeLi was prepared from lithium dispersion and gaseous methyl chloride in toluene (see Table II, Ex. No. 9); additional THF was added.
[3]Loss of methyllithium was determined by NMR.
[4]Total base = total alkalinity or total lithium. Determined by acid - base titration after hydrolysis.
[5]Modified Watson-Eastham titration for active C-Li.
[6]Methyllithium samples were placed in a constant temperature both (40 ± 0.5° C.) for the duration of the test.
[7]Methyllithium samples were placed in the laboratory for the duration of the test. The temperature in the lab ranged from 18 to 26° C. during March, 1986.
[8]Methyllithium samples were placed in the refrigerator. The temperature ranged from 0 to 6° C.

TABLE VII

Thermal Stability[1] of MeLi:1.36 THF[2] in Toluene at Various Temperatures (Ex. No. 10)

| Days | Temp (°C.) | Loss MeLi[3] % (%/day) | Total Base[4] (M) | W.E. Titration[5] (M) | Sample Appearance |
|---|---|---|---|---|---|
| 0 | — | 0 | 1.55 | 1.55 | Light yellow solution no pptn. |
| 5 | 40 ± 0.5[6] | 8.4 | 1.54 | 1.54 | Soln. yellow - pptn. - some gas pressure. |
| 12 | 40 ± 0.5[6] | 28.4 | 1.54 | 1.54 | Solution yellow - slight pptn. - gas pressure |
| 18 | 40 ± 0.5[6] | 47.1 | 1.56 | 1.35 | Soln. red - heavy gas pressure - slight pptn. |
| 27 | 40 ± 0.5[6] | 64.5 (2.39) | 1.58 | 1.23 | Soln. dark red - heavy gas pessure - no pptn. |
| 26 | 22 ± 4[7] | 5.7 (0.21) | 1.53 | 1.54 | Soln. yellow - very slight gas pressure - no pptn. |
| 27 | 3 ± 3[8] | 0(0) | 1.49 | 1.47 | Soln. yellow - no gas pressure - no pptn. |

[1]Method B. Six bottles of MeLi solution were prepared.
[2]MeLi was prepared from lithium dispersion and gasious methyl chloride in toluene (see Table II, Ex. No. 10).
[3]Loss of methyllithium was determined by NMR.
[4]Total base = total alkalinity or total lithium. Determined by acid - base titration after hydrolysis.
[5]Modified Watson-Eastham titration for active C-Li.
[6]Methyllithium samples were placed in a constant temperature both (40 ± 0.5° C.) for the duration of the test.
[7]Methyllithium samples were placed in the laboratory for the duration of the test. The temperature in the lab ranged from 18 to 26° C. during March, 1986.
[8]Methyllithium samples were placed in the refrigerator. The temperature ranged from 0 to 6° C.

TABLE VIII

Solution Stability[1] of Methyllithium in Toluene Containing Varying Amount of THF

| Ex. No. | Temp[2] (°C.) | Days | THF/MeLi[3] (mole ratio) | Concentration (M) | Sample Appearance |
|---|---|---|---|---|---|
| 9 | 3 ± 3 | 28 | 4.26 | 0.90 | Sample changed from yellow to orange. No pptn. |
| 8 | 3 ± 3 | 27 | 3.06 | 1.41 | Sample changed from yellow to orange. No pptn. |
| 4 | 3 ± 3 | 47 | 2.23 | 1.38 | Sample changed from yellow to orange. No pptn. |
| 6 | 3 ± 3 | 28 | 1.73 | 1.59 | Sample remained yellow. No pptn. |
| 10 | 3 ± 3 | 30 | 1.36 | 1.55 | Sample remained yellow. No pptn. |

[1]Solution stability indicates the resistance to produce precipitation due to cold weather.
[2]Samples were placed in the refrigerator. The temperature ranged from 0 to 6° C. during the testing.
[3]THF/MeLi mole ratio was determined by NMR analysis.

TABLE IX

THF/MeCl[1] Yield Effect

| Experiment Number | THF/MeCl[1] Mole Ratio | Reaction Temp. °C. | Yield % |
|---|---|---|---|
| 11 | 0.90[3] | 30 to 40 | 72.0 |
| 15 | 1.10[3] | 30 to 40 | 83.0 |
| 13 | 1.24[3] | 30 to 40 | 83.5 |
| 16 | 1.17[3] | 30 to 40 | 85.2 |
| 10 | 1.30[3] | 30 to 40 | 87.5 |
| 6 | 1.42[3] | 30 to 40 | 87.2 |
| 18 | 1.16[3,7] | 30 to 40 | 87.5 |
| 14 | 1.11[3] | 30 to 40 | 87.7 |
| 17 | 1.14[3,7] | 30 to 40 | 88.9 |
| 20 | 1.20[3] | 30 to 40 | 89.3 |
| 7 | 1.56[3] | 30 to 40 | 75.8 |
| 8 | 1.78[3] | 30 to 40 | 60.4 |
| 9 | 1.89[3] | 30 to 40 | 50.0 |
| Gilman[2] | (3,4,5) | −10 | 23.0 |
| Gilman[2] | (3,4,5) | −10 | 12.0 |
| Gilman[2] | 6.78[5,6] | −10 | 64.0 |

[1]THF/MeCl mole ration indicates the amount of THF present during reaction vs the total moles methylchloride added.
[2]Gilman, H. and GAJ, B. J., J. Org. Chem. 22, 1164 (1957).
[3]Added MeCl as a gas.
[4]Amount of MeCl used not given in paper[2]; however, the THF/Li mole ratio was 9.8, indicating a large excess of THF vs the MeLi formed.
[5]Reaction ran in THF only (no co-solvent).
[6]Added MeCl as a liquid.
[7]2-Methyltetrahydrofuran was used in place of THF.

TABLE X

Solubility of MeLi in Various Lewis Bases and Co-Solvents

| Example Number | Lewis Base Name[1] | Lewis Base/ MeLi[2] | Co-Solvent[1] | Solubilty Limit M[3] |
|---|---|---|---|---|
| (4) | Et$_2$O | 9.24 | None | 1.63 |
| 20 | THF | 1.31 | Benzene | 1.79 |

TABLE X-continued

Solubility of MeLi in Various Lewis Bases and Co-Solvents

| Example Number | Lewis Base Name[1] | Lewis Base/ MeLi[2] | Co-Solvent[1] | Solubilty Limit M[3] |
|---|---|---|---|---|
| 10 | THF | 1.36 | Toluene | 1.55 |
| 13 | THF | 1.52 | Ethylbenzene | 1.36 |
| 14 | THF | 1.45 | Isopropylbenzene | 1.28 |
| 16 | THF | 1.65 | t-Butylbenzene | 0.86 |
| 17 | MTHF | 1.45 | Toluene | 1.37 |
| 18 | MTHF | 1.58 | Isopropylbenzene | 1.01 |
| 15 | THF | 2.50 | Toluene + cyclohexane[5] | 0.46 |
| 3 | THF | 18.46 | Cyclohexane | 0.24 |
| 4 | Et$_2$O | 22.20 | Toluene | 0.17 |
| 19-A | TEA | 2.00 (Theory) | Toluene | 0.00 |
| 19-B | TEA | 6.53 (Theory) | None | 0.00 |
| 22 | DME | 2.43 | Toluene | 0.42 |
| 21-A | TBME | 2.00 (Theory) | Toluene | 0.05 |
| 21-B | TBME | 5.51 (Theory) | None | 0.07 |
| 2-A | None | | Toluene | 0.01 |
| 2-B | None | | Hexane | 0.01 |
| 12[6] | THF | 1.65 | Toluene | 1.42 |

[1]Diethylether (Et$_2$O) Tetrahydrofuran (THF) 2-Methyltetrahydrofuran (MTHF) Triethylamine (TEA) Isopropylbenzene (cumene) Dimethylether (DME) t-Butylmethylether (TBME)
[2]The mole ratio of Lewis base to MeLi was determined by NMR and does critically affect solubility. In some cases theory indicates the amount of Lewis base used vs the amount of solid MeLi present.
[3]This is the tentative solubility limit at ambient was determined by generating excess MeLi for the capacity of the solvents; i.e., more than 7% of the MeLi generated was left on the filter plate.
[4]Comparison Example - 5% "Halide Free" methyllithium in diethylether.
[5]Toluene/MeLi mole ration = 2 with cyclohexane being the balance of the co-solvent.
[6]Ambient solubility limit for MeLi$_{1.0}$·LiBr$_{0.69}$ complex in limited THF/Toluene.

TABLE XI

Thermal Stability of Methyllithium in Various Lewis Base and Co-Solvents

| Example Number | THF/ MeLi[1] Mole Ratio | Aromatic Co-Solvent | MeLi Conc. M | MeLi % Loss/Day at Various °C.[2] | | |
|---|---|---|---|---|---|---|
| | | | | 0 | 24 + 6 | 40 |
| Gilman[6] | 12.24[7] | None | 0.98 | 46[8] | 31[9] | 100[10] |
| 1-A | 2.08 | Toluene | 0.60 | — | 0.00 | — |
| 1-B | 4.22 | Toluene | 0.52 | — | 1.49 | — |
| 8 | 3.06 | Toluene | 1.50 | 0 | 1.35 | 8.63 |
| 9 | 4.26 | Toluene | 0.95 | 0.14 | 2.67 | 15.62 |
| 10 | 1.36 | Toluene | 1.55 | 0 | 0.21 | 2.39 |
| 12[11] | 1.65 | Toluene | 1.43 | 0 | 0 | 0.29 |
| 13 | 1.52 | Ethylbenzene | 1.36 | 0.18[3] | 0.14[3] | 0.85 |
| 14 | 1.45 | Isopropylbenzene[5] | 1.28 | 0.18[3] | 0.16[3] | 0.50 |
| 17 | 1.45[4] | Toluene | 1.37 | 0 | 0.24 | 1.19 |
| 20 | 1.31 | Benzene | 1.79 | 0.05[3] | 0.09[3] | 0.32 |

[1]Determined by NMR method described in a previous report[1].
[2]Determined by NMR[1]. The accuracy of the NMR method was ±4 to 5%. Therefore, data reported in the 0 to 0.2% loss MeLi/day range may be insignificant.
[3]At the end of the test the MeLi solution contained a slight amount of product precipitation which could account for the slight loss.
[4]Used 2-Methyltetrahydrofuran (MTHF) in place of tetrahydrofuran (THF).
[5]Isopropylbenzene = cumene.
[6]Gilman, H. and GAJ, B. J., J. Org. Chem. 22, 1165 (1957).
[7]The initial THF/MeLi mole ratio was 12.24; however, as cleavage took place, the ratio became higher.
[8]Gilman reports the temperature to be 0 to 3° C. The MeLi % loss/day was calculated from Table I[6] as follows:
$$\frac{62.5\% \text{ yield} - 59.5\% \text{ yield}}{62.5\% \text{ yield}} \times 100 \times \frac{24 \text{ hrs.}}{2.5 \text{ hrs.}} = 46.08\% \text{ loss/day.}$$
[9]Gilman reports the temperature to be 25° C. The MeLi % loss/day was calculated from Table I[6] as follows:
$$\frac{43.7\% \text{ yield} - 37.0\% \text{ yield}}{43.7\% \text{ yield}} \times 100 \times \frac{24 \text{ hrs.}}{12 \text{ hrs.}} = 30.66\% \text{ loss/day.}$$
Obviously, the lower rate was due to a reduction of the methyllithium concentration due to previous decomposition.
[10]Gilman reports the temperature to be 65° C. The MeLi % loss/day was calculated from Table I[6] as follows:
$$\frac{37.0\% \text{ yield} - 13.8\% \text{ yield}}{37.0\% \text{ yield}} \times 100 \times \frac{24 \text{ hrs.}}{13 \text{ hrs.}} = 115.75\% \text{ loss/day.}$$
[11]Thermal stability testing of the MeLi.LiBr (1/0.69 mole ratio) complex.

TABLE XII

Preparation of Methyllithium Containing Various Amounts of Dimethylmagnesium Directly from Lithium Metal, Magnesium Metal, and Methylchloride in Aromatic Solvent/THF

| | Reagents | | | | | | Metal Conditioner | |
|---|---|---|---|---|---|---|---|---|
| Ex. No. | Lithium[1] moles | Magnesium[2] moles | Excess[3] Li + Mg Mole % | Methyl-Chloride moles | THF moles | Aromatic Hydrocarbon Solvent (ml) | moles | Contact Time (Hrs) |
| 23 | 2.80 | 0.180 | 19 | 1.33 | 1.21 | Toluene (450) | 0.06 | 4.5 |
| 24 | 0.75 | 0.190 | 3 | 0.55 | 0.60 | Toluene (168) | 0.01 | 0.5 |
| 25 | 0.64 | 0.320 | 28 | 0.50 | 0.60 | Toluene (182) | 0.01 | 1.5 |
| 26 | 1.18 | 0.060 | 10 | 0.59 | 0.65 | Toluene (186) | 0.01 | 4.5 |
| 27 | 0.60 | 0.150 | 15 | 0.39 | 0.58 | Toluene (191) | 0.01 | 4.0 |
| 28 | 2.60 | 0.440 | 10 | 1.58 | 1.74 | Toluene (533) | 0.04 | 3.5 |
| 29 | 1.29 | 0.045 | 3 | 0.67 | 0.71 | Cumene 264 | 0.02 | 14.0 |
| 30 | 1.58 | 0.113 | 10 | 0.82 | 1.26 | Cumene 289 | 0.02 | 6.0 |
| 31 | 4.79 | 0.123 | 12 | 2.25 | 2.71 | Cumene 1330 | 0.02 | 14.0 |

| | Analystical Results | | | | | | |
|---|---|---|---|---|---|---|---|
| Ex. No. | Total Base N | Active Me—M N. | Magnesium Titration M. | Li/Mg Mole Ratio Theory[6] | Li/Mg Mole Ratio Found[7] | THF/Me[5] Mole Ratio | Soluble Chloride[8] M. | Recovered Yield % |
| 23 | 1.95 | 1.92[4] | 0.24 | 6.77 | 6.0 | 1.02 | 0.04 | 91.0 |
| 24 | 1.96 | 2.07[4] | 0.70 | 0.97 | 0.96 | 1.18 | 0.02 | 91.5 |
| 25 | 1.79 | 1.80[5] | 0.77 | 0.00 | 0.33 | 1.28 | 0.01 | 85.5 |
| 26 | 1.81 | 1.76[5] | 0.21 | 8.83 | 6.38 | 1.35 | N.A. | 80.0 |
| 27 | 1.48 | 1.51[5] | 0.50 | 1.00 | 1.02 | 1.66 | 0.01 | 91.0 |
| 28 | 1.97 | 1.97[4] | 0.52 | 1.95 | 1.79 | 1.13 | 0.01 | 87.6 |
| 29 | 1.61 | 1.64[5] | 0.08 | 13.30 | 17.50 | 1.20 | 0.04 | 79.9 |
| 30 | 1.56 | 1.56[4] | 0.12 | 6.10 | 11.00 | 1.90 | 0.08 | 86.5 |

TABLE XII-continued

Preparation of Methyllithium Containing Various Amounts of Dimethylmagnesium
Directly from Lithium Metal, Magnesium Metal, and Methylchloride in Aromatic Solvent/THF

| | | | | | | | | |
|---|---|---|---|---|---|---|---|---|
| 31 | 1.25 | 1.24[4] | 0.05 | 19.00 | 22.80 | 1.25 | 0.06 | 92.7 |

[1]Li contained 0.7 to 1.25 wt. % Na.
[2]Magnesium powder.

[3]Excess Li × Mg calculation: $100\left[\dfrac{\frac{1}{2}\text{ moles Li} \times \text{moles Mg})}{\text{moles MeCl}}\right]$ = mole % excess M.

[4]Determined by the W.E. titration - Watson, S. C.; Eastham, J. F., J. Organomet. Chem. 1967, 9, 165.
[5]Determined by NMR analysis.

[6]Theoretical Li/Mg mole ratio calculation: $\dfrac{\frac{1}{2}\text{ moles Li} - \text{Moles Mg}}{\text{moles Mg}}$ = Li/Mg mole ratio.

[7]Found Li/Mg mole ratio calculation: $\dfrac{\text{Active MeM(N)} - [\text{Mg(M.)} \times 2]}{\text{Mg(M.)}}$ = Li/Mg mole ratio.

[8]Soluble chloride determined by chloride anaysis (Mohr method); found mainly soluble LiCl.

TABLE XIII

PREPARATION OF DIMETHYLMAGNESIUM VIA THE REACTION OF MeCl
AND A MIXTURE OF LITHIUM AND MAGNESIUM IN
TOLUENE CONTAINING A LIMITED AMOUNT OF THF

| | Reagents | | | | | Analytical Results | | | |
|---|---|---|---|---|---|---|---|---|---|
| Ex. No. | Li[2] Moles | Mg[3] Moles | MeCl Moles | THF Moles | Toluene ml | Total Base N. | W.E. Titration[4] N. | Mg Titration[5] M. | Chloride tration M. | Density g/cc |
| 32 | 0.78 | 0.39 | 0.71 | 0.81 | 218 | 2.23 | 2.16 | 1.14 | 0.04 | 0.88 |
| 33 | 3.46 | 1.74 | 3.14 | 3.61 | 964 | 2.15 | 2.15 | 1.02 | 0.03 | 0.88 |

| | NMR | | Atomic Adsorption | | Composition Mole % | | Recovered Yield[7] |
|---|---|---|---|---|---|---|---|
| Ex. No. | Active MeM N. | THF/Me Mole Ratio | Li M. | Mg M. | Me$_2$Mg | MeLi | % |
| 32 | 2.30 | 1.18 | 0.04 | 1.03 | 100 | 0 | 92.6 |
| 33 | 2.06 | 1.23 | 0.05 | 1.03 | 100 | 0 | 93.4 |

[1]The final products were all clear, near water white solution of Me$_2$Mg.
[2]Used lithium dispersion containing 0.7 wt. % Na.
[3]Used Magnesium powder.
[4]The modified Watson Eastham Titration. This titration is not applicable to R$_2$Mg solutions unless slightly more than an equivalent of RLi is added prior to titration.
[5]EDTA Titration for Mg.

TABLE XIV

SYNTHESIS OF Me$_2$Mg/MeMgCl COMPOSITIONS IN TOLUENE/LIMITED THF

| | Reagents | | | | | | Metal Conditioner | |
|---|---|---|---|---|---|---|---|---|
| Ex. No. | Lethium[1] moles | Magnesium[2] moles | Excess[3] Li + Mg Mole % | Methyl- Chloride moles | THF moles | Toluene ml | moles | Contact Time (Hrs) |
| 34 | 0.52 | 0.52 | 11.4 | 0.70 | 0.84 | 190 | 0.009 | 4 |
| 35 | 0.50 | 0.50 | 11.9 | 0.67 | 0.81 | 263 | 0.009 | 24 |

| | Analytical Results | | | | | | | Product Composition Me$_2$Mg/MeMgCl (Mole %) | |
|---|---|---|---|---|---|---|---|---|---|
| Ex. No. | Total Base N. | Active Me—M N. | Magnesium Titration M. | THF/ME[4] Mole Ratio | Soluble[5] Chloride M. | A.A. Analysis[5] Li(M) | A.A. Analysis[5] Mg(M) | Recovered Yield % | Theory | Found |
| 34 | 2.37 | 2.40[4] | 1.42 | 1.21 | 0.77 | 0.10 | 1.49 | 83.9 | 50/50 | 53/47.2 |
| 35 | 1.80 | 1.79[4] | 1.19 | 1.28 | 0.63 | 0.08 | 1.23 | 93.9 | 50/50 | 54/46.3 |

[1]Used Li dispersion containing 0.7% Na.
[2]used magnesium powder.
[3]Excess Li + Mg was calculated by the following equation:

$100\left[\dfrac{(\frac{1}{2}\text{ moles Li} + \text{moles Mg})}{\text{moles MeCl}}\right]$ = mole % excess M.

[4]Determined by NMR analysis.
[5]Soluble chloride determined by chloride analysis and is mainly soluble LiCl.
[6]Determined by Atomic Adsorption Spectroscopy.

TABLE XV

SUMMARY TABLE COMPARISON OF THERMAL STABILITY OF MeLi/Me$_2$Mg
COMPOSITIONS AND MeLi IN LIMITED THF/AROMATIC SOLVENT
AT VARIOUS TEMPERATURES

| | Composition mole % | | Aromatic Co- | MeM Con- centration | THF/Me[1] | | MeM Average % Loss/Day[2] at Various Temps | |
|---|---|---|---|---|---|---|---|---|
| Example No. | MeLi | Me$_2$Mg | solvent | N. | Mole Ratio | 3 ± 3° C. | Room Temp | 40 ± 0.5° C. |
| 23 | 86 | 14 | Toluene | 1.95 | 1.04 | 0 | 0.34[4] | 1.05 |

TABLE XV-continued

SUMMARY TABLE COMPARISON OF THERMAL STABILITY OF MeLi/Me$_2$Mg COMPOSITIONS AND MeLi IN LIMITED THF/AROMATIC SOLVENT AT VARIOUS TEMPERATURES

| Example No. | Composition mole % MeLi | Composition mole % Me$_2$Mg | Aromatic Co-solvent | MeM Concentration N. | THF/Me[1] Mole Ratio | $3 \pm 3°$ C. | MeM Average % Loss/Day[2] at Various Temps Room Temp | $40 \pm 0.5°$ C. |
|---|---|---|---|---|---|---|---|---|
| 10 | 100 | 0 | Toluene | 1.55 | 1.36 | 0 | 0.21[3] | 2.39 |
| 24 | 49 | 51 | Toluene | 1.96 | 1.18 | 0 | 0[3] | 0 |
| 25 | 25 | 75 | Toluene | 1.80 | 1.28 | 0 | 0[3] | 0 |
| 14 | 100 | 0 | Cumene[5] | 1.45 | 1.45 | 0.18[6] | 0.16[4] | 0.50 |
| 28 | 64 | 36 | Toluene | 1.97 | 1.20 | 0 | 0[4] | 0.13 |
| 29 | 94.5 | 5.5 | Cumene[5] | 1.45 | 1.20 | 0 | 0[3] | 0 |

[1]Det'd by NMR. Accuracy of method 4 to 5%.
[2]Testing period = 29–33 days.
[3]Samples tested in winter (lab temp. ranged from 16 to 22°)
[4]Samples tested in summer (lab temp. ranged from 18 to 30°)
[5]Isopropylbenzene
[6]Product precipitation rather than decomposition accounts for the loss shown.

TABLE XVI

COMPARISON SOLUBILITY OF METHYLLITHIUM AND MeLi/Me$_2$Mg COMPOSITION AT VARIOUS TEMPERATURES

| Ex. No. | MeLi/ Me$_2$Mg Mole % | THF/Me Mole Ratio | Aromatic Co-solvent | Solubility Limit[1] N. Room Temp | 0 C. | −20 C. |
|---|---|---|---|---|---|---|
| 29 | 94.5/5.5 | 1.20 | Cumene | 1.60 | 1.34 | 0.92 |
| 30 | 91/9 | 2.11 | Cumene | 1.60 | 1.31 | 0.93 |
| 31 | 95.8/4.2 | 1.25 | Cumene | N.A. | 1.10 | 0.67 |
| 14 | 100/0 | 1.45 | Cumene | 1.28 | 0.66 | 0.66 |
| 10 | 100/0 | 1.36 | Toluene | 1.55 | 1.55 | N.A. |
| 23 | 86/14 | 1.04 | Toluene | 1.95 | 1.95 | N.A. |

[1]NMR analysis of clear samples taken after 30 days at indicated temperature.

TABLE XVII

THERMAL STABILITY[1] AND SOLUBILITY OF DIMETHYLMAGNESIUM[2] IN TOLUENE CONTAINING A LIMITED AMOUNT OF THF (1.23 eq/Me GROUP) AT VARIOUS TEMPERATURES (EX. No. 33)

| Date Tested | Temperature C. | No. Days | NMR Analysis[3] MeM N. | % Loss | Average % Loss/Day | Total Base N. | Magnesium Titration M. | Sample Appearance |
|---|---|---|---|---|---|---|---|---|
| 6/16/87 | Start | 0 | 2.06 | — | — | 2.15 | 1.02 | Clear, colorless solution. |
| 6/30/87 | $40 \pm 0.5$[4] | 14 | 2.09 | — | — | 2.15 | 1.03 | Clear, colorless solution. Very slight residue. No gas pressure. |
| 7/14/87 | $40 \pm 0.5$ | 28 | 2.16 | 0 | 0 | 2.15 | 1.10 | Clear, colorless solution. Very slight residue. No gas pressure. |
| 7/14/87 | $25 \pm 5$[5] | 28 | 2.12 | 0 | 0 | 2.16 | 1.07 | Clear, colorless solution. No precipitation. No gas pressure. |
| 7/14/87 | $3 \pm 3$[6] | 28 | 2.15 | 0 | 0 | 2.16 | 1.08 | Clear, colorless solution. No precipitation. No gas pressure. |
| 7/17/87 | $-18 \pm 4$[7] | 31 | — | — | — | — | — | Clear, colorless solution. No precipitation. No gas pressure. |

[1]Method B. Six bottles of Me$_2$Mg solution were prepared. In order to avoid contamination each bottle was sampled only once, then discarded.
[2]Me$_2$Mg was prepared from methylchloride, lithium, and magnesium metals in limited THF and toluene.
[3]Active methyl-M and MeCl were determined by NMR analysis.
[4]Samples wre placed in a constant temperature bath ($40° C. \pm 0.5°$ C.) for the tests.
[5]Sample placed in the Organic Laboratory. The temperature varied from 20 to 30° C. during June and July.
[6]A sample was placed in the refrigerator (temp. range = 0 to 6° C.).
[7]A sample was placed in the freezer compartment of the refrigerator. Temp. range = −16 to −20° C.

We claim:

1. An organometallic composition comprising (1) 50 to 99 mole percent of an organometallic composition (a) of the formula RM in which R is selected from methyl, ethyl and propyl and M the metal is an alkali metal selected from dithium, sodium and potassium; (2) 50 to 1 mole percent of an organometallic composition (b) of the formula R$^1$R$^2$M$^1$ in which R$^1$ and R$^2$ are independently selected from methyl, ethyl and propyl and M$^1$ the metal is selected from magnesium, barium, and calcium; (3) a hydrocarbon solvent; (4) 0.05 to 2 mole equivalents of a Lewis Base selected from tetrahydrofuran and methyltetrahydrofuran per mole of organometallic composition; and (5) 1 to 100 mole percent of lithium halide, LiX, based on the organometallic composition.

2. A composition of claim 1 wherein the alkali metal is selected from lithium and sodium.

3. A composition of claim 1 wherein the R, R$^1$ and R$^2$ are selected from methyl and ethyl groups.

4. A composition of claim 1 wherein the mole percent of RM is between 50 and 99 while the mole percent or R$^1$R$^2$M$^1$ is between 50 and 1 and the total mole percent is 100.

5. A composition of claim 4 wherein RM is methyllithium and R$^1$R$^2$M$^1$ is dimethylmagnesium.

6. A composition according to claim 2 wherein RM is methyllithium, the Lewis Base is tetrahydrofuran and the mole ratio of tetrahydrofuran to methyllithium is from 0.1:1 to 2:1.

7. A composition according to claim 5 wherein the Lewis Base is tetrahydrofuran and the mole ratio of tetrahydrofuran to methyllithium is from 1.1:1 to 1.5:1.

8. The composition of claim 1 wherein the mole percent of RM is between 90 and 99 mole percent, the mole percent of $R^1R^2M^1$ is between 10 and 1 mole percent, RM is methyllithium, $R^1R^2M^1$ is dimethylmagnesium and the liquid hydrocarbon solvent is an aromatic hydrocarbon.

9. The composition of claim 8 wherein the mole percent of RM is between 91 and 95.8 mole percent and the mole percent $R^1R^2M$ is between 9 and 4.2 and the hydrocarbon solvent is a liquid aromatic hydrocarbon.

10. The composition of claims 4, 8, or 9 wherein the aromatic hydrocarbon solvent is cumene.

* * * * *